United States Patent [19]

Anderson et al.

[11] Patent Number: 5,360,897

[45] Date of Patent: *Nov. 1, 1994

[54] IMMUNOGENIC CONJUGATES OF STREPTOCOCCUS PNEUMONIAL CAPSULAR POLYMER AND TOXIN OR IN TOXIAD

[75] Inventors: Porter W. Anderson; Ronald J. Eby, both of Rochester, N.Y.

[73] Assignee: The University of Rochester, Rochester, N.Y.

[*] Notice: The portion of the term of this patent subsequent to Jun. 16, 2004 has been disclaimed.

[21] Appl. No.: 819,305

[22] Filed: Jan. 9, 1992

Related U.S. Application Data

[63] Continuation of Ser. No. 423,081, Oct. 18, 1989, Pat. No. 5,097,020, which is a continuation of Ser. No. 859,975, May 5, 1986, Pat. No. 4,902,506, which is a continuation-in-part of Ser. No. 511,048, Jul. 5, 1983, Pat. No. 4,673,574, which is a continuation-in-part of Ser. No. 298,102, Aug. 31, 1981, abandoned.

[51] Int. Cl.$^5$ .................... A61K 39/385; C07K 17/02
[52] U.S. Cl. .................... 530/403; 530/405; 530/406; 530/807; 424/197.11; 424/244.1; 424/831; 424/832
[58] Field of Search ............... 530/395, 405, 406, 807; 530/403; 424/92, 88

[56] References Cited

U.S. PATENT DOCUMENTS

| | | | |
|---|---|---|---|
| 4,196,192 | 4/1980 | Kuo | 424/92 |
| 4,210,641 | 7/1980 | Brossard et al. | 424/180 |
| 4,220,717 | 9/1980 | Kuo | 435/101 |
| 4,356,170 | 10/1982 | Jennings et al. | 424/92 |
| 4,411,888 | 10/1983 | Klipstein et al. | 424/92 |
| 4,451,446 | 5/1984 | Vandevelde et al. | 424/92 |
| 4,459,286 | 7/1984 | Hilleman et al. | 424/87 |
| 4,496,538 | 1/1985 | Gordon | 424/92 |
| 4,663,160 | 5/1987 | Tsay et al. | 424/87 |
| 4,673,574 | 6/1987 | Anderson | 424/92 |
| 4,693,891 | 9/1987 | Collins et al. | 424/92 |
| 4,761,283 | 8/1988 | Anderson | 424/92 |
| 4,762,713 | 8/1988 | Anderson | 424/92 |
| 4,771,127 | 9/1988 | Cryz et al. | 530/395 |
| 4,808,700 | 2/1989 | Anderson et al. | 530/403 |
| 4,902,506 | 2/1990 | Anderson et al. | 424/92 |
| 5,097,020 | 3/1992 | Anderson et al. | 530/403 |

FOREIGN PATENT DOCUMENTS

| | | |
|---|---|---|
| 60129 | 8/1982 | European Pat. Off. . |
| 98581 | 1/1984 | European Pat. Off. . |
| 109688 | 5/1984 | European Pat. Off. . |

OTHER PUBLICATIONS

Cryz, et al., 1986, Infec. and Immun. 52(1):161–165.
Cryz, et al., 1987, Infec. and Immun. 55(7):1547–1551.
Cryz et al., 1987, Rev. Infec. Dis. 9(5):S644–S649.
Fenwick and Osburn, 1986, Infec. and Immun. 54(2):583–586.

(List continued on next page.)

*Primary Examiner*—Kay K. Kim
*Attorney, Agent, or Firm*—Pennie & Edmonds

[57] ABSTRACT

An immunogenic conjugate which is the reductive amination product of an immunogenic capsular polymer fragment having at least one reducing group and derived from a bacterial capsular polymer of a bacterial pathogen, and a bacterial toxin or toxoid. The invention also relates to methods for the preparation of the conjugates, a vaccine containing the conjugates which elicits effective levels of anti-capsular polymer antibodies in humans. Also disclosed are methods for inducing active immunization against systemic infection in young mammals caused by bacterial pathogens comprising the administration of an immunogenic amount of the above-described conjugate. In a preferred embodiment, the capsular polymer fragment prior to conjugation has at least one aldehyde group at each end of the fragment. The final conjugate made with such capsular polymers has a lattice or network structure, and provides extremely high levels of anti-capsular polymer antibodies in infants.

7 Claims, No Drawings

OTHER PUBLICATIONS

Larm and Scholander, 1977, Carbo. Res. 58:249–251.
Lee and Lin, 1981, Rev. Infec. Dis. 3:S51–S60.
Lugowski, et al., 1983, Infec. and Immun. 42:1086–1091.
Lugowski, et al., 1986, J. Immun. 95:187–194.
Tsay and Collins, 1984, Infec. and Immun. 45(1):217–221.
Wachsmann, et al., 1986, Infec. and Immun. 52(2):408–413.
Geyer et al., Med. Microbiol. Immunol. 165:271 (1979).
Schneerson et al., J. Exptl. Med. 152:361 (1980).
Schwartz et al., Arch. Biochem. Biophys. 181:542 (1977).
Schneerson et al., *New Developments With Human and Veterinary Vaccines*, Alan R. Liss, Inc., New York, pp. 77–94 (1980).
Stein et al., J. Immunol. 128(3): 1350–1354 (1982).
Galanos et al., European J. Biochem. 8:332–36 (1969).
Zamenhof et al., J. Biol. Chem. 203: 695–704 (1953).
Beuvery et al., Infect. Immun. 37(1): 15–22 (1982).
Lin et al., Immunol. 46: 333–42 (1982).
Schneersen et al., Progress in Allergy, Karger, Basel, vol. 33, pp. 144–158 (1983).
Anderson, Infect. Immun. 39(1): 233–38 (1983).
Tsay et al., Abstract 3348, Federation Proceedings, vol. 42, No. 4 (Mar. 5, 1983).
Tsay et al., Abstract 217, Federation Proceedings, Abstract 43: 1453 (1984).
Tsay et al., Infect. Immun. 45(1): 217 (1984).
Chu et al., Infect. Immun. 40(1): 245–256 (1983).
Ovary et al., Proc. Soc. Exp. Biol. Med. 114: 72–76 (1963).
Jennings et al., J. Immunol. 127: 1011–1018 (1981).
Uchida et al., Science 115: 901–903 (1972).

IMMUNOGENIC CONJUGATES OF STREPTOCOCCUS PNEUMONIAL CAPSULAR POLYMER AND TOXIN OR IN TOXIAD

This is a continuation of application Ser. No. 07/423,081, filed Oct. 18, 1989, now U.S. Pat. No. 5,097,020, which is a continuation of application Ser. No. 06/859,975 filed May 5, 1986, currently U.S. Pat. No. 4,902,506, which is a continuation-in-part of application Ser. No. 06/511,048 filed Jul. 5, 1983, currently U.S. Pat. No. 4,673,574, which is a continuation-in-part of application Ser. No. 06/298,102, filed Aug. 31, 1981, currently abandoned, all of which are incorporated by reference herein.

FIELD OF THE INVENTION

This invention relates to the field of novel vaccine compositions, processes for producing them and methods for immunization of young warm-blooded animals, including humans, against infections and disease caused by bacteria, including, for example, *Haemophilus influenzae* type b, *Escherichia coli*, *Neisseria meningitidis* serogroups A and C, *Streptococcus pneumoniae* serotypes 3, 6, 12, 14, 19, 23 and 51, and *Pseudomonas*.

BACKGROUND OF THE INVENTION

It is known that purified bacterial capsular polymers (CP) generally are immunogenic in mature humans and animals and can be used as vaccines against the corresponding systemic infections. As used in this application, the term "capsular polymers" refers to sugar-containing polymers, such as polymers of sugars, sugar acids, amino sugars, polyhydric alcohols and sugar phosphates, and does not refer to amino acid-containing polymers. These "capsular polymers" are frequently referred to in the medical literature as "capsular polysaccharides", though they may contain linkages other than glycosidic linkages and constituents other than sugars such as those listed above.

The capsular polymers of different bacteria vary widely in immunogenicity in the first year of human life. Some are moderately active, such as *Streptococcus pneumoniae* serotype 3 and *Neisseria meningitidis* serogroup A. The susceptibility to systemic infection by encapsulated bacteria is greater in the first year of life. The immunogenic response to many bacterial capsular polymers in children is age dependent, i.e., immunocompetence to CP increases to adult levels by about six years of age.

Among the inactive CP are those of *Haemophilus influenzae* type b, *Streptococcus pneumoniae* serotypes 6 and 12, and *Neisseria meningitidis* serogroup C. Examples of CPs which give an intermediate response in infants are *Streptococcus pneumoniae* serotypes 19 and 51.

INTACT CAPSULAR POLYMERS AS ANTIGENS IN VACCINES

Various investigators have isolated and purified intact capsular polymers which may be useful in or as vaccines. For example, U.S. Pat. No. 4,220,717 describes a process for the isolation and purification of immunologically active polyribosyl ribitol phosphate (PRP) from the capsular polymer of *H. influenzae* b. Additionally, U.S. Pat. No. 4,210,641 relates to polysaccharide extracts of *H. influenzae* having an apparent molecular weight greater than 200,000 daltons and composed principally of galactose, glucose and mannose and containing a small amount of osamines.

Several researchers have utilized these and other intact capsular polymers in formulations to achieve better immunological responses. For example, U.S. Pat. No. 4,196,192 discloses a vaccine containing purified intact PRP and whole *Borderella pertussis* bacteria. This approach to increasing immunogenicity resulted in enhanced levels of anti-PRP and anti-pertussis antibodies in young mammals.

VACCINES CONTAINING CONJUGATES

Other researchers have studied conjugation of capsular polymers to carrier proteins in an effort to enhance antibody formation by the so-called "carrier effect". For example, Schneerson et al., J. Exper. Med. 152:361–376 (1980), describes *H. influenzae* b polymer-protein conjugates disclosed to confer immunity to invasive diseases caused by *H. influenzae* b. The reference documents the age-related immunological behavior of capsular polymers in infants and seeks to overcome this age-dependence by conjugation of the intact capsular polymer with a variety of proteins, including serum albumins, *Limulus polyphemus* hemocyanin and diphtheria toxin. The method of conjugation involves the use of a linking agent such as adipic dihydrazide.

Geyer et al., Med. Microbiol. Immunol. 165:171–288 (1979), prepared conjugates of certain *Klebsiella pneumoniae* capsular polysaccharide fragments to a nitrophenylethylamine linker by reductive amination, and the derivatized sugar was then attached to proteins using azo coupling.

SUMMARY OF THE INVENTION

The present invention relates to the covalent attachment of capsular polymer fragments derived from bacterial capsular polymers to bacterial toxins or toxoids by means of reductive amination. As used in the present application, the term "toxoid" means a form of a toxin which has the antigenicity of the toxin without its toxicity.

The immunogenic conjugates of the invention are prepared by first forming reducing end groups on fragments of the capsular polymers and reacting these with amine groups of the bacterial toxin or toxoid by reductive amination. The reducing end groups may be formed by any suitable method, including selective hydrolysis, e.g., by acids or enzymes, or by oxidative cleavage, e.g., by periodate or related oxygen acids. The conjugation is preferably achieved by reductive amination in an aqueous solution containing cyanoborohydride anions.

The immunogenic conjugates of the invention may be formulated with a pharmaceutically acceptable carrier to produce a vaccine which elicits effective levels of anticapsular antibody formation in young mammals, including humans. The vaccine may be utilized to induce active immunization against systemic infection in young mammals caused by the respective encapsulated bacteria by administering an immunogenic amount of the conjugate to the mammal.

The immunogenic conjugates have been found to be less age dependent than the capsular polymers alone, and are useful for the active immunization of very young warm-blooded mammals against systemic infections by the respective encapuslated bacteria.

Furthermore, the immunogenic conjugates of the invention do not contain potentially toxic linking agents, such as adipic dihydrazide or p-nitro-phenyl-ethylamine, which have been used in conjugating carbohydrate to protein.

Finally, the immunogenic conjugates of the invention contain fragments of capsular polymers, not intact capsular polymers. The highly repetitive structure of capsular polymers may be in part responsible for their failure to expand the capacity for antibody production in infants. A conjugate of intact (highly polymerized) CP and protein may only partially overcome the immunologic disadvantages of CP alone.

On the other hand, the use of capsular polymer fragments on a carrier may circumvent the disadvantages of the repetitive structure. Additionally, the CP determinants of a conjugate having CP fragments are on the average closer to the carrier than are the CP determinants of conjugates having intact CP, and this proximity to carrier may be necessary for a more effective "carrier effect".

A further advantage lies in the use, for the protein carrier, of a bacterial toxin or toxoid against which children are routinely vaccinated, e.g., tetanus or diphtheria. Desired immunity to the toxin or toxoid is induced along with immunity against the pathogens associated with the capsular polymer.

It is to be understood that reference throughout this specification to any theory to explain the results described is not to limit the scope of the invention. Independent of the method by which the invention functions, the results and advantages described herein may be achieved by reference to the following detailed description.

DETAILED DESCRIPTION OF THE INVENTION

The conjugates of the invention are formed by reacting reducing end groups of the capsular polymer fragment to primary amino groups of a bacterial toxin or toxoid to yield antigenic determinants of the capsular polymer covalently linked to the carrier protein. The reducing groups may be formed by selective hydrolysis or specific oxidative cleavage, or combinations of both.

Antigenic fragments with at least one reducing end can be generated from capsular polymers by a variety of methods, depending upon the structural features of the particular capsular polymer. Limited oxidative cleavage by periodate (or related reagents such as paraperiodic acid, sodium metaperiodate and potassium metaperiodate) will leave aldehydic termini; such an approach will be limited to polymers having vicinal dihydroxy groups. Hydrolysis of a glycosidic linkage produces a reducing sugar terminus. Such hydrolysis can be most specifically accomplished enzymatically by glycosidases, but this application would be restricted to a relatively few capsular polymers, e.g., *Streptococcus pneumoniae* 8, for which glycosidases are known. Acidic hydrolysis is commonly used for hydrolysis of glycosidic linkages. The utility of this approach would be limited if the polymer contains acid-sensitive non-glycosidic linkages or if the polymer contains acid-Sensitive branch linkages important to the antigenic specificity. Base hydrolysis can also be used if the polysaccharide contains base labile bonds to the glycosidic carbon such as phosphate, sulfate or ester linkages. The utility of this approach would be limited if the polymer contained other base sensitive non-glycosidic linkages.

Certain capsular polymers may lack vicinal dihydroxy groups which are susceptible to cleavage by periodate (or related oxygen acids). However, prior hydrolysis of such capsular polymers with acid, base or enzyme may liberate vicinal dihydroxy groups which would be susceptible to oxidative cleavage generally. For example, removal of pyruvic acid, acetates, formates, etc., by acid hydrolysis, or removal of sialic acid by enzyme cleavage, may be done prior to the oxidative cleavage step. This, of course, would be limited in application to those capsular polymers in which the groups modified are not important to antigenic specificity.

Where the capsular polymer is hydrolyzed to form capsular polymer fragments having only one functional aldehyde group, conjugation to a multifunctional protein (having at least two free amine groups) results in a conjugate in which a single molecule of the protein has one or more capsular polymer fragments covalently attached. It can readily be seen that the number of capsular polymer fragments attached to the protein can be routinely regulated by changes in the conditions of the conjugation reaction, including the relative concentration of capsular polymer fragments to protein and the overall concentration of the reactants. Of course, regulation of any reaction parameter, e.g., time, temperature, pH, etc., which affects the reactivity or rate of reaction will alter the final composition and structure of the conjugate.

When the capsular polymer fragment has at least one functional aldehyde group located on each end of the fragment (for example, as the result of oxidative cleavage of vicinal dihydroxy groups of a non-cyclic residue), conjugation to a multifunctional protein can result in several types of conjugate. For example, conjugation of such reactants has the potential for forming a lattice or network structure, particularly where there are many free amines on the protein and capsular fragments are in low molar excess to protein. The degree of cross-linking and overall size of the network or lattice can be regulated. by routine variation of the conditions of the conjugation reaction.

The conjugation os carried out according to the reductive amination process of Schwartz and Gray, Arch. Blochem. Biophys. 181:542–549 (1977). Briefly, the process involves reacting the reducing capsular polymer fragment and bacterial toxin or toxoid in the presence of cyanoborohydride ions, or another reducing agent which will not reduce the reducing ends of interest nor adversely affect the toxin or toxoid or capsular polymer.

The cyanoborohydride ions (or their equivalent) act primarily as a mild selective reducing agent of the Schiff base intermediate formed between the carbonyl groups of the capsular polymer fragment and amino groups of the protein. A secondary effect of such ions is the slower reduction of any active aldehyde groups remaining on the capsular polymer fragments after conjugation has occurred. Optionally, after conjugation, additional cyanoborohydride ions (or their equivalent) may be added to reduce such unreacted free aldehyde groups. It is often desirable to add the stronger reducing agent, borohydride ion, after conjugation to ensure adequate reduction of the remaining carbonyl groups.

Thus, unlike previously employed conjugation procedures wherein the active molecules are joined by a linking agent which forms a part of the final product, the reducing anions utilized herein are not incorporated into the final product. This is important from the standpoint of controlling the potential toxicity (i.e., undesired immunogenicity) of the final product. Evidence of covalent linkage is demonstrated by the fact that the association between, for example, a PRP moiety and the carrier protein persists despite salting-out of the protein in the presence of 8M urea, which has a great ability to disrupt non-covalent bonds.

Suitable carrier proteins are those which are safe for administration to young mammals and immunologically effective as carriers. Safety would include absence of primary toxicity and minimal risk of allergic complications. Diphtheria and tetanus toxoids fulfill these criteria; that is, suitably prepared, they are non-toxic and the incidence of allergic reactions is well documented. Though the risk of allergic reaction may be relatively significant for adults, it is minimal for infants.

In the "carrier effect" a weak antigen, by being attached to a stronger antigen as carrier (e.g., a heterologous protein), becomes more immunogenic than if it were presented alone. If an animal is previously immunized with the carrier alone, it may become "primed" for an enhanced response not only to the carrier antigen but also the attached weaker antigen. Infants are routinely immunized with tetanus and diphtheria toxoids. Thus, they would be primed for subsequent presentation of a capsular polymer antigan conjugated to either of these toxoids.

In general, any heterologous protein could serve as a carrier antigen. However, certain bacterial toxins such as tetanus and diphtheria may have an additional advantage in that they are composed of two portions, one of which (the "binding" subunit) has a strong affinity for binding to mammalian cell surfaces. Conceivably, conjugation to such a "binding" protein would permit the carried antigen to more effectively initiate responses in cells of the immune system.

The carrier proteins to which the capsular polymer is conjugated may be native toxin or detoxified toxin (toxoid). Also, by relatively recent mutational techniques, one may produce genetically altered proteins which are antigenically similar to the toxin yet non-toxic. These are called "cross reacting materials", or CRMs. $CRM_{197}$ is noteworthy since it has a single amino acid change from the native diphtheria toxin and is immunologically indistinguishable from it.

A culture of *Corynebacterium diphtheria* strain C7 ($\beta$197), which produces $CRM_{197}$ protein, has been deposited with the American Type Culture Collection, Rockville, Md. and has been assigned accession number ATCC 53281.

Conjugation of capsular polymer to native toxin may reduce toxicity, but significant toxicity may remain. Thus, further detoxification would be required. Conventional detoxification of protein toxins employs formalin, which reacts with free amino groups of the protein. Residual toxicity may still be a concern. Furthermore, spontaneous retoxification is possible with any particular lot of vaccine and remains an issue of concern with this approach.

Alternatively, native toxin may be detoxified with formalin to produce conventional toxoid before conjugation to capsular polymer. However, the prior formalin treatment reduces the number of free amino groups available for reaction with the reducing groups of the capsular polymer fragment. CRMs, thus, have significant advantages in that they have no inherent toxicity yet none of their amino groups is occupied by the formalin. A further advantage is that no biohazards exist in working with CRMs.

In the case of $CRM_{197}$, which is immunologically identical to native toxin, treatment with formalin (though there is no need to detoxify) greatly enhances the immunological response. It is thought that this is due to stabilization of the molecule against degradation by mechanisms of the body and/or aggregation by cross-linking (immunogenicity of particles increases with size).

For all of the above reasons, tetanus and diphtheria toxins are prime candidates for carrier proteins, yet there are others which may also be suitable. Though these others may not have the history of safety found with diphtheria and tetanus, there may be other overwhelming reasons to use them. For instance, they may be even more effective as carriers, or production economics may be significant. Other candidates for carriers include toxins or toxoids of pseudomonas, staphylococcus, streptococcus, pertussis and enterotoxigenic bacteria, including *Escherichia coli.*

Suitable carrier media for formulating a vaccine include sodium phosphate-buffered saline (pH 7.4) or 0.125M aluminum phosphate gel suspended in sodium phosphate-buffered saline at pH 6 and other conventional media. Other pharmaceutical carriers suitable for use in vaccines are known in the art.

Generally, vaccines of the invention containing from about 5 to about 100 $\mu g$, preferably about 10 to 50 $\mu g$, are suitable to elicit effective levels of antibody against the capsular polymer in young warm-blooded mammals. Of course, the exact dosage would be determined by routine dose/response experimentation. Several small doses given sequentially would be expected to be superior to the same amount of conjugate given as a single injection.

The vaccines of the invention may be administered by injection to warm-blooded mammals of any age and are especially adapted to induce active immunization against systemic infections in young mammals caused by the pathogens *Haemophilus influenzae* type b, *Escherichia coli,* pneumococcus, meningococcus, streptococcus and pseudomonas.

The following are non-limiting examples of methods for the preparation of exemplary immunogenic conjugates of the present invention and their use in vaccines.

EXAMPLE: GENERATION OF LARGE, MEDIUM AND SMALL FRAGMENTS OF PRP CONTAINING REDUCING END GROUPS AND CONJUGATION TO $CRM_{197}$

The capsular polymer of *Haemophilus influenzae* type b is a linear polymer with the repeating unit [-3-$\beta$-D-ribosyl(1-1) ribitol(5-phosphate)-] (PRP). Generally, acid hydrolysis of PRP is carried out until the ratio of total to reducing ribose has dropped to 25 or below. The resulting mixture of size fragments may be fractionated by molecular sieve column chromatography to isolate the desired size range of fragments for conjugation. The method for obtaining fragments is as follows:

a. A sample of sodium PRP, (nucleic acid content 0.006%) containing 28.6 milligrams ribose was dissolved with distilled water to make a total volume of 9.2 ml in a 125-ml erlenmeyer flask and chilled in ice.
b. 1.02 ml of 0.1N $H_2SO_4$ was added.
c. Duplicate samples of 0.01 ml of the acidified PRP were transferred to test tubes held on ice (0-minute)

d. The flask was transferred to a boiling-water bath for 3 minutes, then chilled in an ice-water bath.

e. Step c was repeated (3-minute sample).

f. The samples were assayed for reducing power by the alkaline ferricyanide method standarized with D-ribose.

g. Based on the result (see Table 1), step d was repeated.

h. Step c was repeated (6-minute samples).

i. Step f was repeated.

TABLE 1

| Samples | Nanomoles of reducing ribose (av) | Ratio, total ribose/reducing ribose |
|---|---|---|
| 0-min | 0.42 | 493 |
| 3-min | 6.08 | 34.0 |
| 6-min | 9.66 | 21.4 |

The result (see Table 1) indicated that, assuming the sole mode of hydrolysis had been at the (1-1) glycosidic linkage, after 6 minutes the number-average chain length was 21.4 monomeric units, i.e., (ribitol-5-phosphate-3-ribose).

j. 0.102 ml 1N NaOH was added, and the pH was estimated by indicator paper (about pH 6).

k. The neutralized hydrolysate was lyophilized.

l. Bio-Gel P10 (Bio-Rad, Inc.) was equilibrated in 0.1M triethylammonium acetate and poured into a 1.5 cm diameter chromatographic column, giving a gel-bed height of 98 cm.

m. The lyophilized material (step k) was rehydrated with 2.7 ml water, and 0.3 ml of 1M triethylammonium acetate was added. This solution was applied to the column and elution was carried out with collection of 3.5 ml fractions.

n. The elution of ribosyl residues was determined by assay of 0.005-ml samples of each fraction for riboes content by the orcinol reaction with D-ribos. as standard.

o. Fractions were combined into 3 pools, L, M, and S as indicated in Table 2, and the pools were assayed for total ribose and reducing ribose:

TABLE 2

| Pool | Fractions contained | Total ribose, micromoles | Ratio, total ribose/reducing ribose | Est. Mn* | Range of Ve/Vo of fraction |
|---|---|---|---|---|---|
| L | 15–18 | 577 | 31.2 | 11,000 | ≦1.08 |
| M | 19–23 | 744 | 18.6 | 6800 | 1.09–1.38 |
| S | 24–34 | 1180 | 9.1 | 3400 | 1.39–1.99 |

*on the assumption that the sole hydrolysis was glycosidic.

p. The pools were lyophilized, re-hydrated with 10 ml water, re-lyophilized, and re-hydrated with 1.5 ml water. 1.2 ml of the last solutions were transferred to microcentrifuge tubes and lyophilized in preparation for the conjugation reactions.

Conjugation of $CRM_{197}$ to Reducing Fragments of PRP a. To the microcentrifuge tubes containing lyophilized fragments, L, M, and S, and to an empty tube (C or control) were added potassium phosphate buffer pH 8, 2.7 milligrams $CRM_{197}$, and 4 milligrams sodium cyanoborohydride, such that the final volume was 0.2 ml and the phosphate-buffer was at 0.2M.

b. The tubes were incubated at 37° C. with daily mixing.

c. After 18 days the tubes were centrifuged 2 minutes at 7000 G.

d. After determination that the majority of protein was in the precipitates, the precipitates were washed four times with ≦1 ml water.

e. The washed precipitates were made 8M in urea and warmed to 50° C., dialyzed against saline overnight at 4° C., and centrifuged. The supernates were separated and made 95% saturated in ammonium sulfate, held overnight at 4° C., and centrifuged. The resulting precipitates were washed 3 times with 0.4 ml of 95% saturated ammonium sulfate, and suspended with 1 ml water. These colloidal suspensions were labeled $CRM_{197}$-PRP-L, -M, -S, and $CRM_{197}$-C, respectively.

f. The preparations were assayed for protein by means of the Folin phenol reaction with bovine albumin as standard and for ribosyl residues with the orcinol reaction and D-ribose as standard. The results are given in Table 4. The preparations were assayed for PRP antigenic activity by their ability (at concentrations of 50 micrograms protein/ml) to inhibit the binding of labeled native PRP to human anti-PRP antibody (Table 3).

TABLE 3

| Preparation tested | % Antigen bound | antigenic activity, ng PRP equiv./μg protein |
|---|---|---|
| none | 28.1 | — |
| >native PRP, 0.5 ng | 6.7 | — |
| >native PRP, 5 ng | 0.94 | — |
| $CRM_{197}$-C | 34.3 | 0.0 |
| $CRM_{197}$-PRP-S | 2.0 | 0.1 |
| $CRM_{197}$-PRP-M | 2.5 | 0.08 |
| $CRM_{197}$-PRP-L | 3.9 | 0.006 |

Thus, all the tested conjugates of $CRM_{197}$ with PRP fragments were antigenically active, while the control preparation in which $CRM_{197}$ was exposed to cyanoborohydride in the absence of PRP fragments was inactive as expected.

The preparations were assayed for immunogenicity in rabbits in comparison with high molecular weight purified PRP, and the results are given in Table 4. Rabbits given the PRP control or the $CRM_{197}$-C control made barely detectable increases in anti-PRP antibody. Rabbits given any of the three $CRM_{197}$-PRP conjugates made progressive increases after each injection; the titers after the third injection were 1000-fold greater than prior to immunization. In an experiment not illustrated a simple mixture of $CRM_{197}$ and PRP fragment preparation L was assayed in rabbits and found not to elicit anti-PRP antibody.

TABLE 4

ANTI-PRP ANTIBODY RESPONSE TO CONJUGATED AND CONTROL VACCINES OF WEANLING RABBITS PRIMED WITH ORDINARY DIPTHERIA TOXOID*

| | Rabbit Vaccine** | Pentose/ protein ratio | Anti-PRP Antibody, ng/ml, at age in weeks | | | |
|---|---|---|---|---|---|---|
| | | | 7*** | 8*** | 9*** | 10 |
| 1 | PRP(MW $10^5$) | | <10 | 12 | 28 | 40 |
| 2 | " | | <10 | <10 | 27 | 26 |
| 3 | $CRM_{197}$-C (control) | — | 35 | 25 | 31 | 36 |
| 4 | " | | 16 | 34 | 40 | 48 |
| 5 | $CRM_{197}$-PRP-S | 0.015 | 19 | 980 | 26,000 | 49,000 |
| 6 | " | | <10 | 84 | 23,000 | 31,000 |
| 7 | $CRM_{197}$-PRP-M | 0.0069 | <10 | 37 | 2,500 | 11,000 |
| 8 | " | | 23 | 11,000 | 49,000 | 150,000 |
| 9 | $CRM_{197}$-PRP-L | 0.0020 | 14 | 73 | 3,700 | 26,000 |
| 10 | " | | <10 | 340 | 9,800 | 76,000 |

*The rabbits were New Zealand Whites obtained from Dutchland Farms immediately after weaning. At six weeks of age each was injected subcutaneously (s.c.) with 40 Lf of diptheria toxoid (Massachusetts Dept. of Public Health) contained in 0.5 ml of 0.0125 M aluminum phosphate pH 6 (alum).
**The PRP vaccine was 30 µg PRP lot 17 contained in 0.1 ml saline. The other vaccines were 25 µg protein contained in 0.5 ml alum.
***Injections of the indicated vaccine were given (s.c.) immediately after bleeding. There were two rabbits per vaccine. Listed are individual titers, determined by radioantigen binding with $^3$H-labeled native PRP.

The protective potential of the anti-PRP antibodies induced by the conjugates was evaluated by testing the bactericidal activity of the rabbit sera of Table 4. The bactericidal titers were determined against H. influenzae b strain Eag by the methods of Anderson et al., J. Clin. Inv., 65: 885–891 (1980). Table 5 shows that before vaccination the sera were unable to kill the bacterial (reciprocal titers <2). After three injections the reciprocal titers of the rabbits receiving the $CRM_{197}$-PRP conjugates had risen to 16 or greater while titers of the rabbits receiving the $CRM_{197}$ control remain at <2.

TABLE 5

Bacterial Titers Against H. influenzae b Strain Eag of Sera of Weanling Rabbits Vaccinated With $CRM_{197}$ or Its Conjugates With Oligosaccharides S, M, and L of PRP*

| | | Reciprocal serum dilution for >90% Killing | |
|---|---|---|---|
| Rabbit | Vaccine given | Pre-vaccination | After 3 injections |
| 3 | $CRM_{197}$ control | <2 | <2 |
| 4 | $CRM_{197}$ control | <2 | <2 |
| 5 | $CRM_{197}$-PRP-S | <2 | 128 |
| 6 | $CRM_{197}$-PRP-S | <2 | ≧256 |
| 7 | $CRM_{197}$-PRP-M | <2 | 16 |
| 8 | $CRM_{197}$-PRP-M | <2 | 64 |
| 9 | $CRM_{197}$-PRP-L | <2 | 64 |
| 10 | $CRM_{197}$-PRP-L | <2 | 32 |

*Same vaccinations as described in Table 4.

EXAMPLE: VARIATION OF PRP FRAGMENT RATIO TO $CRM_{197}$

In this example, the ratio of PRP fragment S to $CRM_{197}$ was varied and the conservation of antigenic activity of the $CRM_{197}$ component was examined in addition to the PEP component.

Preparation of $CRM_{197}$-PRP-S#2, A and B a. To microcentrifuge tubes A and B were added 0.15 ml each of the solution of fragments S described above, i.e., steps o and p. The solutions were lyophilized.
b. Tube A received 0.015 ml 2M potassium phosphate buffer pH 8, 0.1 ml of $CRM_{197}$ 5 mg/ml in 0.01M sodium phosphate buffer pH 7, and 0.015 ml of sodium cyanoborohydride 200 mg/ml.
c. Tube B received 0.002 ml of the pH 8 buffer and 0.1 ml of the $CRM_{197}$ solution. The resulting solution was lyophilized. The solids were suspended with 0.015 ml water, and 0.002 ml of the pH 8 buffer were added.
d. Tubes A and B were incubated at 37° C. for 13 days. To tube B an additional 0.002 ml of cyanoborohydride was added. Both tubes were incubated at 37° C. for an additional 3 days. (Note that due to the reduced reaction volume, the concentrations of reactants in B were higher than A.)
e. To A was added 0.06 ml water and 0.8 ml saturated ammonium sulfate (SAS). To B was added 0.175 ml water and 0.8 ml SAS.
f. The tubes were incubated 1 hour at 0° C. and centrifuged 20 minutes at 8000 G. The supernates were removed.
g. The precipitates were washed by suspension in 1 ml of 80% SAS, centrifugation at 8000 G 20 minutes, and removal of the supernates.
h. The precipitates were suspended with 0.1 ml water, and 0.4 ml SAS was added.
i. Same as step f.
j. Same as step g.
k. The precipitate in B was dissolved with 0.084 ml 9.5M urea (estimated final concentration 8M); 0.1 ml water and 0.8 ml SAS were added, and the precipitate was isolated as in step f. This precipitate was washed as in step g.
l. The precipitates in A and B were suspended with 0.2 ml water. The suspensions were separated into soluble (s) and insoluble (i) fractions by centrifugation 30 minutes at 8000 G, and the s fractions (supernates) were made 0.01M sodium phosphate buffer pH and reserved.
m. The i fractions (precipitates) were rendered more soluble as follows: they were made 8M in urea, which was then gradually removed by dialysis against 0.01M sodium phosphate buffer pH 7. The resulting solutions were recombined with the respective s fractions.
n. Preparations A and B were tested for protein content with the Folin phenol reagent and for PRP antigenic activity by the assay described above. Both had PRP activity; B exceeded A by about 13-fold, as shown below:

| Preparation | ng PRP equivalence/μg protein |
|---|---|
| $CRM_{197}$-PRP-S#2,A | 0.038 |
| $CRM_{197}$-PRP-S#2,B | 0.50 | o. Preparations A and B were tested for CRM antigenicity (activity as diphtheria toxoid (DT)) by inhibition of the binding of antibody to a sample of purified DT furnished by the Massachusetts Department of Public Health. Both had activity roughly equal to the DT on a weight basis; B exceeded A by about 4-fold, as shown below.

| Inhibitor tested | Antibody bound, $A_{400}$ | μg DT equivalence per μg protein |
|---|---|---|
| None | 2.43 | |
| DT, 0.5 μg/ml | 2.56 | |
| DT, 5 μg/ml | 1.93 | |
| DT, 50 μg/ml | 0.96 | |
| $CRM_{197}$-PRP-S#2,A,50 μg/ml | 1.25 | 0.52 |
| $CRM_{197}$-PRP-S#2,B,5 μg/ml | 1.67 | 2.0 | p. Preparations A and B were suspended in alum at 16 μg protein 1 ml, and three 0.5 ml injections were given to rabbits in the protocol described in Table 4 (except the animals were 8 weeks old at the onset and not primed by previous injections of diphtheria toxoid). The sera were tested for antibodies in the binding assay described in step o. Both A and B elicited antibodies to DT as well as to PRP, as shown in Table 6. Separate control experiments showed that similar rabbits housed in the same quarters did not display such increases in anti-DT antibody values in the absence of being injected with $CRM_{197}$ preparations.

TABLE 6

| Rabbit | Injected | Assay for antibody to | Antibody values at age | | | |
|---|---|---|---|---|---|---|
| | | | 8 wk | 9 wk | 10 wk | 11 wk |
| 5 | A | PRP, ng/ml | 47 | 60 | 210 | 13,500 |
| | | DT, $A_{400}$ | 0.136 | 0.168 | 1.28 | 3.81 |
| 6 | A | PRP | 21 | 25 | 19 | 420 |
| | | DT | 0.072 | 0.049 | 0.262 | 3.23 |
| 7 | A | PRP | <20 | 20 | 2000 | 10,500 |
| | | DT | 0.155 | 0.134 | 0.155 | 0.676 |
| 3 | B | PRP | <20 | 27 | 1600 | 4900 |
| | | DT | 0.075 | 0.061 | 0.227 | 2.45 |
| 8 | B | PRP | 23 | <20 | 2900 | 26,000 |
| | | DT | 0.065 | 0.023 | 0.231 | 2.07 |

EXAMPLE: CONJUGATION OF VERY SMALL FRAGMENTS OF PRP TO DIPHTHERIA TOXIN, DIPHTHERIA TOXOID AND $CRM_{197}$

Generation of Very Small Fragments of PRP Containing Reducing End Groups a. A 12 ml solution of PRP lot 20 was made 0.1M in HCl at 0° C. and sealed in a glass flask (0 minute).
b. The flask was transferred to a boiling-water bath for 4 minutes, then chilled in an ice water bath.
c. A small amount of resulting white colloid was removed by extraction with ether and the resulting clear solution was lyophilized.
d. Bio-Gel P10 (Bio Rad, Inc.) was equilibrated in 0.01M ammonium acetate and poured into a 1.5 cm diameter chromatographic column, giving a gel bed height of 98 cm.
e. The lyophilized material was rehydrated with 1.5 ml water and neutralized with $NH_4OH$. This solution was applied to the column and the elution was carried out.
f. Fragments eluting at Ve/Vo range of 2.0–2.4 were collected and designated fraction vs.
g. Steps a–f were repeated to double the supply of fraction vs.
h. The combined vs fractions were lyophilized, rehydrated to yield 4 ml of a solution containing a total of 47 μmoles of reducing sugar activity when assayed by the alkaline ferricyanide method standardized with D-ribose.

Preparation of Conjugates of PRP-vs Fragments to Native Diphtheria Toxin, Native Diphtheria Toxoid and $CRM_{197}$ The following proteins are used as carriers in the present example:
(1) DTx—purified diphtheria toxin, lot 1, obtained from the Massachusetts Public Health Biologic Laboratories. Partial detoxification is accomplished by the linking to PRPvs. Residual toxicity is removed by formalin treatment in the presence of lysine by the method of Pappenheimer et al., Immunochem. 9:891 (1972).
(2) DTd—conventional (formal) toxoid, lot DCP-27, also obtained from the Massachusetts laboratories.
(b 3) $CRM_{197}$—antigenically mutated version of the toxin protein, antigenically indistinguishable from toxin but non-toxic.

The conjugation method is as follows:
a. Protein, potassium phosphate buffer (pH 8.0 at 25° C.) and PRPvs were combined in glass centrifuge tubes in the manner set out below.

| Solution | Protein | Buffer | PRPvs |
|---|---|---|---|
| (1) | 30 mg DTx | 0.24 μmol | 20 μmol |
| (2) | 30 mg DTd | 0.24 μmol | 20 μmol |
| (3) | 10 mg $CRM_{197}$ | 0.08 μmol | 6.7 μmol | b. The solutions were lyophilized, and the lyophiles were dissolved with $NaCNBH_3$ solution, 2% w/v in water as tabulated below.

| Solution | 2% $NaCNBH_3$ |
|---|---|
| (1) | 1.2 ml |
| (2) | 1.2 ml |
| (3) | 0.4 ml | c. The tubes were incubate at 37° C.
d. After 14 days, four volume-equivalents of saturated ammonium sulfate were added. These suspensions were held 3 hours at 0° C., then centrifuged 20 minutes at 9000 G.

e. The precipitates were washed twice each with 10 ml of neutral 70% saturated ammonium sulfate.

f. The washed precipitates were dissolved with a minimal volume of 9.5M urea and dialyzed against 0.067M sodium phosphate buffer, pH 7.8.

Formalin Treatment of the Conjugates

The conjugates were further dialyzed against sodium phosphate buffer which also contained 0.025M lysine. (Small samples were reserved for toxicity testing prior to formalinization).

b. Formalin was added to a final concentration of 0.2% v/v.

c. After 17 days incubation at about 24° C. the solutions were extensively dialyzed against the sodium phosphate buffer.

d. Centrifugation was performed to remove small amounts of insoluble material.

Processing to Achieve Final Container Products a. Antigen solutions (1)–(3) in isotonic sodium phosphate buffer were passed through 0.22-micron "Millex" filter units (Millipore Corp.) and injected into bottles containing sterile phosphate buffered saline.

b. The preparations were assayed for protein using the Lowry method.

c. Thimerosal was filtered and injected into the solution as 1/100 volume of a freshly made 1% w/v solution. Samples of 10 ml were taken for a sterility test. The bottles were attached to a manually operated sterile single use filling device (Multiple Additive Set, Travenol Laboratories). 2-ml glass vials were filled, stoppered, sealed, and immediately transferred to storage at 4° C.

Assays on Conjugate Preparations a. Phosphate content of the protein fraction

PRP is composed of the repeating unit ribosyl-ribitol-phosphate. Thus colorimetric assay of phosphate in the fraction precipitable by 5% trichloracetic acid (TCA) is a sensitive index of the incorporation of PRP fragments into the protein.

Samples containing 100 μg protein were made 5% in TCA in a volume of 3 ml, held 20 minutes on ice, and centrifuged 15 minutes at 4° C. at G. The precipitates were washed with an additional 3 ml of 5% TCA, then with 5 ml ethanol. The washed precipitates were ashed to convert organic phosphate to inorganic phosphate (Pi), and the Pi was quantified by the method of Chen et al., Anal. Chem., 28:1756 (1956). The results were as follows:

| Sample | nmol Pi/ μg protein | Implied average no. of PRP repeating units/protein |
|---|---|---|
| (1) DTx-PRPvs | 0.11 | 6.8 |
| (2) DTd-PRPvs | 0.10 | 6.2 |
| (3) CRM$_{197}$-PRPvs | 0.10 | 6.2 | b. Electrophoretic Analysis

Samples of the conjugated antigens were analyzed by mercaptoethanol-sodium dodecyl sulphate-polyacrylamide gel electrophoresis (ME-SDS-PAGE) in the same gel alongside the respective starting carrier protein preparations.

DTd-PRPvs, like the DTd, displayed a disperse band at MW 61,000 daltons. In contrast, DTx-PRPvs and CRM$_{197}$-PRPvs differed greatly from the starting proteins. The protein of these two conjugates collected either at the beginning of or in the stacking gel (4% acrylamide) or at the beginning of the separating gel (10% acrylamide). Thus, the conjugates appear to have been converted into macromolecular aggregates, presumably by cross-linking from the formalin treatment. DTd-PRPvs also contains some aggregated material.

c. PRP Antigen Equivalence Per Unit Protein

The capacity of the conjugates to bind anti-PRP antibody was determined by the inhibition of the binding of labeled PRP by human anti-PRP antiserum, calibrated with PRP lot 19. (Because protein-bound polymer fragments cannot be assumed to bind to antibody in a weight-equivalent fashion to the high molecular weight polymer, quantitative chemical composition cannot be inferred from these data.)

| Sample | % Inhibition of $^3$H-PRP bound | ng PRP equivalence/ μg protein |
|---|---|---|
| PBS control | (0) | — |
| PRP 19, 0.5 ng/ml | 6.7 | — |
| PRP 19, 5 ng/ml | 32 | — |
| PRP 19, 50 ng/ml | 90 | — |
| DTx-PRPvs, 5 μg protein/ml | 24 | 0.5 |
| DTd-PRPvs, 5 μg protein/ml | 48 | 2.2 |
| CRM$_{197}$-PRPvs, 5 μg protein/ml | 38 | 1.4 | d. Diphtheria Toxoid Antigenic Equivalence Per Unit Protein

Retention of the capacity of the preparations to react with anti-DTd antibody was determined by inhibition of an enzyme-linked immunosorbent assay (ELISA) in which purified DTd is attached to the assay tube (solid phase). Inhibition of antibody binding to the attached DTd is calibrated by the same DTd used in the fluid phase.

| Sample | % Inhibition of Antibody Binding | μg DTd equivalence/ μg protein |
|---|---|---|
| PBS control | (0) | — |
| DTd, 5 μg/ml | 24 | — |
| DTd, 50 μg/ml | 50 | — |
| DTx-PRPvs, 50 μg protein/ml | 46 | 0.68 |
| DTd-PRPvs, 50 μg protein/ml | 58 | 2.1 |
| CRM$_{197}$-PRPvs, 50 μg protein/ml | 26 | 0.11 | e. Diphtheria Toxic Activity

Samples of the original DTx and the conjugate DTx-PRPvs before and after formalin treatment were titrated for toxic activity by injection into the skin of a non-immune adult rabbit. DTx at doses of 0.002 μg and 0.02 μg produced the expected dermal lesions. DTx-PRPvs prior to formalin treatment produced dose-dependent lesions such that 0.2 μg was approximately equal to 0.002 μg DTx (100-fold reduction in toxicity by the conjugation). After formalin treatment, lesions were not generated by doses as high as 2 μg (at least 1000-fold reduction relative to DTx). Doses up to 2 μg of conjugates DTd-PRPvs and CRM$_{197}$-PRPvs were tested similarly and generated no lesions.

f. Induction of Anti-PRP Antibody Responses in Weanling Rabbits, Measured by Radioantigen Binding The antigens were mixed with an aluminum phosphate adjuvant (0.0125M Al, pH 6) such that a 0.5 ml dose contained 25 µg protein. Two rabbits (for each antigen) were given three weekly injections beginning at age 7 weeks; the rabbits had been injected with DTd alone at age 5 weeks, for a hypothetical "carrier priming" effect. All the animals (rabbits 1-6) had anti-PRP rises in an anamnestic pattern, with titers of at least 10 µg/ml after the third vaccination. Antigens $CRM_{197}$-PRPvs and DTd-PRPvs were also tested in pairs of rabbits that had not been "primed" with DTd. These (rabbits 7-10) produced strong anti-PRP reponses similar to those in the "primed" rabbits.

g. Induction of Anti-DTd Antibody Response in Weanling Rabbits, Measured by ELISA The anti-DTd antibody responses in the same "unprimed" rabbits (7-10) of the preceding subsection are as follows: Rises were roughly 10-fold after the second injection and another 2- to 5-fold after the third.

h. Sterility of the Sample Preparations

The samples were found to be sterile as determined using Fluid Thioglycollate (BBL cat. no. 11260, lot D4D LKL) as the growth medium.

EXAMPLE: USE OF PRP FRAGMENTS CONJUGATED TO DIPHTHERIA TOXOID AND $CRM_{197}$ AS VACCINES IN YOUNG HUMANS

Two groups of 8 children in the age range of 1 to 2 years old (and specifically exempting children receiving routine vaccination with diphtheria toxoid protein at age 18 months) were given primary and secondary vaccinations as follows: Group I received injections of $CRM_{197}$-PRPvs preparation as described in the preceding section (25 g protein in saline, subcutaneously); Group II received injections of DTd-PRPvs, preparation as described in the preceding section (25 µg protein in saline, subcutaneously).

In the first visit, pre-vaccination blood specimens were taken; the child was vaccinated, then observed for 20 minutes for any sign of an anaphylactic reaction. In the second visit the procedure of the first visit was repeated. In the third visit, a post-secondary blood specimen was taken. Two of the children, one from each group, after consultation with the parents, were given a third vaccination to try to raise the antibody against PRP to protective levels. The interval between vaccinations was $1 \pm \frac{1}{2}$ month.

Group III consisted of children about 18 months old receiving a vaccine simultaneously with diphtheria toxoid protein in a separate site. This group contained 2 children; one received the $CRM_{197}$-PRPvs vaccine, the other received the DTd-PRPvs vaccine.

Symptoms were recorded for four successive days, with measurements of temperature, notation of behavioral indications of systemic illness and observations of inflammation at the injection site. These symptoms are summarized in Table 7.

TABLE 7

ADVERSE REACTIONS TO PRP-VS CONJUGATES TO $CRM_{197}$ AND FORMAL DIPHTHERIA TOXOID

| Vaccine | Symptom | Primary | Secondary | Tertiary |
|---|---|---|---|---|
| $CRM_{197}$-PRPvs | Fever | 1/8 | 0/8 | 0/1 |
| | Unusual behavior | 0/8 | 0/8 | 0/1 |
| | Local inflammation | 1/9* | 2/9 | 0/1 |
| | Local pain | 1/9* | 1/9 | 0/1 |

TABLE 7-continued

ADVERSE REACTIONS TO PRP-VS CONJUGATES TO $CRM_{197}$ AND FORMAL DIPHTHERIA TOXOID

| Vaccine | Symptom | Primary | Secondary | Tertiary |
|---|---|---|---|---|
| DTd-PRPvs | Fever | 0/8 | 0/8 | 0/1 |
| | Unusual behavior | 0/8 | 0/8 | 0/1 |
| | Local inflammation | 1/9* | 0/9 | 0/1 |
| | Local pain | 1/9 | 1/9 | 0/1 |

*Includes one child who received diphtherai toxoid protein simultaneously in a separate site. No local symptoms were found. Systemic symptoms are not noted since these could not be distinguished from an effect of the diphtheria toxoid protein vaccine.

After $CRM_{197}$-PRPvs vaccination, one child had mild fever (99.8° F.) on the evening of primary vaccination; there was an instance of mild local inflammation once each after a primary, a secondary, and the one tertiary vaccination. After DTd-PRPvs there was an instance of local inflammation after one primary and one secondary vaccination. The administration of the vaccines was otherwise apparently free of adverse reactions.

Serum Antibody Reponses

Antibodies to PRP as well as IgG antibodies to diphtheria toxoid were determined. After vaccination with $CRM_{197}$-PRPvs a consistent anti-PRP response pattern was seen. See Table 8. There was a distinct rise after the primary injection, usually an even larger rise after the secondary injection, and a large rise after the one tertiary. The final titers greatly exceeded those that have been produced by vaccination with PRP alone and greatly exceeded the accepted estimated protective minimal level of 0.15 µg/ml. The enhanced response was particularly evident in the four children under 18 months of age, where the response to PRP alone is generally inadequate for protection, and the geometric mean of the final titers in these four (8.4 µg/ml) is 175 times that found after vaccination of children 12-17 months old with PRP vaccine alone. The child receiving the primary vaccination simultaneously with diphtheria toxoid protein vaccine also had an excellent response.

IgG antibodies to diphtheria toxoid increased in 6 of 8 children (as well as in the 9th, who also received diphtheria toxoid as part of the treatment). The antibody levels often increased so greatly that the dilution of post-vaccination serum used (1/1000) was insufficient to show the full extent of the rise.

After vaccination with DTd-PRPvs anti-PRP responses generally increased after both primary and secondary vaccination. (See Table 9). However, there were two children (12 and 14 month old) in whom no response was detected; and one child did not approach the protective level until given a third injection. The child receiving the primary vaccination simultaneously with diphtheria toxoid protein had an excellent response. Rises in IgG antibody to the diphtheria component were found in all children.

TABLE 8

ANTIBODY RESPONSE TO $CRM_{197}$-PRPvs

| Subject | Age at primary vaccination | Serum sample | Serum antibody, µg/ml | |
|---|---|---|---|---|
| | | | anti-PRP | IgG anti-DTd |
| 1 | 12 mo | pre-vac | 2.0 | 1.1 |
| | | post-1 | 4.5 | >10 |

TABLE 8-continued

ANTIBODY RESPONSE TO CRM$_{197}$-PRPvs

| Subject | Age at primary vaccination | Serum sample | Serum antibody, μg/ml | |
|---|---|---|---|---|
| | | | anti-PRP | IgG anti-DTd |
| | | post-2 | 18 | >10 |
| 2 | 13 mo | pre-vac | <0.006 | 0.38 |
| | | post-1 | 0.040 | 1.7 |
| | | post-2 | 0.35 | 2.2 |
| | | post-3 | 4.8 | 1.9 |
| 3 | 14 mo | pre-vac | <0.020 | 4.5 |
| | | post-1 | 0.12 | 3.3 |
| | | post-2 | 2.0 | 4.3 |
| 4 | 16 mo | pre-vac | 0.025 | 0.06 |
| | | post-1 | 0.92 | 5.7 |
| | | post-2 | 29 | 9.1 |
| 5 | 27 mo | pre-vac | 0.025 | 3.0 |
| | | post-1 | 10 | >10 |
| | | post-2 | 58 | >10 |
| 6 | 29 mo | pre-vac | 0.13 | 6.1 |
| | | post-1 | 22 | 6.9 |
| | | post-2 | 180 | 7.4 |
| 7 | 30 mo | pre-vac | 2.2 | 6.5 |
| | | post-1 | 28 | >10 |
| | | post-2 | 50 | >10 |
| 8 | 30 mo | pre-vac | 1.3 | 4.8 |
| | | post-1 | 6.5 | 10 |
| | | post-2 | 78 | 10 |
| 9 | 18 mo* | pre-vac | 0.34 | 3.1 |
| | | post-1 | 1.4 | >10 |
| | | post-2 | 8.2 | >10 |

*First injection of CRM$_{197}$-PRPvs given simultaneously with diphtheria toxoid protein vaccine in a separate site.

TABLE 9

ANTIBODY RESPONSE TO DTd-PRPvs

| Subject | Age at primary vaccination | Serum sample | Serum antibody, μg/ml | |
|---|---|---|---|---|
| | | | anti-PRP | IgG anti-DTd |
| 1 | 12 mo | pre-vac | <0.020 | 0.060 |
| | | post-1 | <0.020 | 10 |
| | | post-2 | <0.020 | 10 |
| 2 | 12 mo | pre-vac | 0.055 | 0.03 |
| | | post-1 | 0.080 | 3.1 |
| | | post-2 | 1.8 | 10 |
| 3 | 13 mo | pre-vac | <0.006 | 1.1 |
| | | post-1 | <0.006 | 10 |
| | | post-2 | 0.023 | 10 |
| | | post-3 | 0.120 | 10 |
| 4 | 14 mo | pre-vac | <0.020 | 3.0 |
| | | post-1 | <0.020 | 5.1 |
| | | post-2 | <0.020 | 3.8 |
| 5 | 19 mo | pre-vac | 0.060 | 8.0 |
| | | post-1 | 0.12 | 10 |
| | | post-2 | 0.76 | 10 |
| 6 | 26 mo | pre-vac | <0.020 | 6.9 |
| | | post-1 | 0.060 | 10 |
| | | post-2 | 0.94 | 10 |
| 7 | 27 mo | pre-vac | 1.4 | 6.1 |
| | | post-1 | 7.4 | 10 |
| | | post-2 | 21 | 10 |
| 8 | 28 mo | pre-vac | <0.020 | 8.7 |
| | | post-1 | 0.63 | 10 |
| | | post-2 | 8.0 | 10 |
| 9 | 18 mo* | pre-vac | 1.9 | 0.11 |
| | | post-1 | 2.9 | 10 |
| | | post-2 | 11 | 10 |

*First injection of DTd-PRPvs given simultaneously with diphtheria toxoid protein vaccine in a separate site.

This example shows that injections of conjugates of the *H. influenzae* b capsular polymer fragment to diphtheria toxoid and CRM$_{197}$ is apparently harmless. CRM$_{197}$-PRPvs vaccination gave a clear indication of an enhancement of the anti-PRP response by the carrier effect - appreciated not only by the high titers but by the rises after secondary vaccination.

DTd-PRPvs had a less impressive enhancement. A likely explanation is that while CRM$_{197}$-PRPvs is a multimolecular aggregate, DTd-PRPvs is present mainly in unimolecular form similar to the original toxoid.

EXAMPLE: CONJUGATION OF CAPSULAR POLYMER FRAGMENTS OF STREPTOCOCCUS PNEUMONIAE TO CRM$_{197}$

Several other bacteria resemble *H. influenzae* b in that they cause sepsis and meningitis, particularly in infants; they have polymer capsules, antibodies to which are protective; and their capsular polymers are immunogenic in mature humans but not in infants. An important example is *Streptococcus pneumoniae* (SP) serotype 6. It causes not only the life-threatening infections mentioned above but also is a highly prevalent cause of otitis media in children. (Gray et al., J. Infect. Dis. 142: 923–33, 1980).

The approach described for PRP is also applicable to any capsular polymer in which reducing groups can be generated by selective hydrolysis with retention of antigenic specificity. In the following non-limiting example, capsular polymer fragments were made from the Sp. 6 capsular polymer by selective acid hydrolysis and were conjugated to CRM$_{197}$. The product retained antigenic specificity for both the Sp capsular polymer and the CRM$_{197}$ component.

Generation of Reducing Fragments From Capsular Polymers (CP)

1. A sample of the CP of Sp. 6 (Danish type 6A, Eli Lilly Co.) was assayed for total hexose by the phenol-sulfuric acid method standardized with D-glucose and for reducing activity by the alkaline ferricyamide method also standardized with D-glucose.
2. Pyrex tube received 3.3 mg Sp. 6 CP dissolved with 0.66 ml water. The sample was chilled to 0° C., 0.073 ml of 0.1N HCl were added, and the tube was sealed.
3. The tube was immersed 10 minutes in a boiling water bath, then rechilled to 0° C. A small sample was assayed for reducing activity as described in step 1:

| CP | Time heated at 100° C. | Total hexose/ reducing hexose |
|---|---|---|
| Sp. 6 | 0 minutes | >350 |
| | 10 minutes | 6.5 |

4. The hydrolyzed preparation (minus the 2% used for assay) was lyophilized. The dried material was dissolved with 0,1 ml water, transferred to microcentrifuge tube, and lyophilized again.

Conjugation to CRM$_{197}$

1. To the re-dried hydrolysate was added 0.004 ml of 2M potassium phosphate buffer pH 8 and 1 mg of CRM$_{197}$ dissolved in 0.2 ml of 0.01M sodium phosphate buffer pH 7. The resulting mixture was lyophilized and resuspended with 0.05 ml water (estimated total volume 0.063 ml).
2. To the tube was added 0.007 ml of sodium cyanoborohydride at 200 mg/ml, and the preparation was incubated 18 days at 37° C.
3. 0.6 ml 80% saturated ammonium sulfate (SAS) was added.

4. The tube was incubated 1 hour at 0° C. and centrifuged 15 minutes at 8000 G; the supernate was removed.
5. The precipitate was washed by suspension in 0.6 ml of 80% SAS buffered at pH 8 with 0.01M sodium phosphate, followed by centrifugation 15 minutes at 8000 G.
6. The precipitate was suspended with 0.02 ml of 0.5M $Na_2HPO_4$ and 0.2 ml 9.5M urea.
7. 1 ml SAS was added, the precipitate was isolated as in step 4 and suspended in urea at about 8M as in step 6.
8. The suspension was centrifuged 15 minutes at 8000 G.
9. The supernate was separated and dialyzed against 0.01M sodium phosphate buffer pH 7 at 4° C.
10. The dialyzed preparations, designated $CRM_{197}$-Sp.6 was assayed for the following:
    protein by the Folin phenol reaction;
    Sp antigenicity by inhibition of binding of antibody to radiolabeled Sp CP (as described for PRP in Table 3);
    $CRM_{197}$ antigenicity by the inhibition of antibody binding to diphtheria toxoid (DT) (as described in step o of the description of $CRM_{197}$-PRP-S#2); and
    anti-CP immunogenicity by inhibition of the binding of antibody to diphtheria toxoid (DT) (as described in step p of the description of $CRM_{197}$-PRP-S#2). See Table 7.

| Preparation | ng CP equivalance/ µg Protein | µg DT equivilance/ µg protein |
|---|---|---|
| $CRM_{197}$Sp. 6 | 0.4 | 0.36 |

TABLE 10
ANTI-CP IMUNOGENIC RESPONSE OF WEANLING RABBITS WITH CONTROLS AND CONJUGATES OF *STREPTOCOCCUS PNEUMONIAE* SEROTYPE 6 FRAGMENTS OF $CRM_{197}$

| Rabbit | Vaccinated With* | Percent $^{14}$C-CP Bound in Samples at age** | | | |
|---|---|---|---|---|---|
| | | 6 wk | 8 wk | 10 wk | 11 wk |
| 1 | Sp 6 CP, 25 µg | 6 | 6 | 7 | 7 |
| 2 | " | 6 | 13 | 13 | 11 |
| 3 | Sp 6 bacteria 25 µg | 4 | 10 | 12 | 16 |
| 4 | " | 8 | 12 | 22 | 21 |
| 5 | $CRM_{197}$ Sp 6, 25 µg | 4 | 6 | 30 | 49 |
| 6 | " | 4 | 8 | 30 | 54 |

*Injected subcutaneously just prior to taking serum samples. Serum samples were taken at age 6, 8 and 10 weeks.
**25 µl serum incubated with 2 nCi $^{14}$C-labelled CP.

EXAMPLE; CONJUGATION OF PRP FRAGMENTS PRODUCED BY OXIDATIVE CLEAVAGE TO $CRM_{197}$

In this example, the final conjugate comprises two components; fragments of PRP of reasonably well defined chain length covalently linked to the non-toxic, immunogenic diptheria toxin $CRM_{197}$. In this example, conditions of the periodate oxidation and isolation by ultrafiltration govern the chain length of the capsular polymer (PRP) fragments.

The conjugate is constructed with capsular polymer fragments having an aldehyde group at both ends of the fragment. Thus, each fragment can be covalently linked to CRM at both ends, presumably at lysine residues of CRM. The structure of the product can, therefore, be considered a "lattice."

The composition and presumably the structure of the conjugate can be altered by changing the concentration of the two components in the conjugating chemical reaction.

The PRP used to produce the PRP fragments for the PRP-CRM conjugate vaccine had the following specifications:

| Protein content | <1.0% |
|---|---|
| Nucleic acids content | ≦1.0% |
| Endotoxin (LAL) | <1.0 EU/µg PRP |
| Molecular size (Kd) | <0.3 (Sepharose CL-48) |
| | <0.6 (Sepharose CL-28) |

Production Methods for PRP Fragments a. A solution of PRP (5-7 mg/ml) was cooled to 4° C. and 2M phosphate buffer pH 7.0 was added to make the final concentration 0.2M phosphate.
b. Sodium metaperiodate (0.2-0.3 moles $IO_4$/mole PRP) was added with rapid mixing, and the solution was incubated at 4° C. overnight in the dark.
c. The reaction solution was ultrafiltered using a H1P30 hollow fiber (Amicon, 30,000 Mw cut-off). The retentate was washed 4 times with 250 ml of saline. The filtrates were combined and ultrafiltered using a H1P10 hollow fiber (Amicon, 10,000 Mw cut-off). The retentate was washed 4 times with 250 ml of saline. The retentate was then concentrated to >35 mg of PRP/ml.
d. The retentate was analyzed for ribose by orcinol assay and reducing groups by alkaline ferricyanide assay. A small aliquot of the retentate was analyzed on a Biogel P-100 column (0.7×25 cm) using 0.15M saline as elutant and analyzing each of the fractions by orcinol and alkaline ferricyanide assay. The analysis showed that the retentate material was composed of oligosaccharides having a DP between 15 and 30 with a weight average DP of about 20.

For capsular polymer fragments prepared by oxidative cleavage chain length (DP) is defined as (ribose units/reducing groups)×2.

Two batches of periodate oxidized PRP were fractionated as in part d and were characterized as follows:

| | SACCHARIDE CHAIN LENGTH | | | |
|---|---|---|---|---|
| | DP of Fraction | | % of Total | |
| Fraction No. | BATCH #2 | BATCH #3 | BATCH #2 | BATCH #3 |
| 14 | 36.5 | 41.0 | 2.7 | 5.9 |
| 15 | 24.1 | 32.5 | 11.0 | 9.4 |
| 16 | 25.3 | 24.5 | 13.2 | 11.8 |
| 17 | 25.4 | 22.8 | 14.4 | 14.3 |
| 18 | 23.2 | 20.2 | 13.6 | 14.6 |
| 19 | 20.2 | 19.0 | 11.9 | 14.2 |
| 20 | 20.4 | 17.7 | 9.3 | 12.4 |
| 21 | 16.1 | 16.0 | 6.7 | 10.0 |
| 22 | 11.7 | 12.3 | 7.2 | 7.1 |

CRM-PRP Conjugation a. CRM protein was dissolved in 0.2M sodium phosphate buffer (pH 7.0) at a final concentration of 10 mg/ml.

b. Lyophilized oligosaccharide was reconstituted in distilled water, an appropriate quantity (average DP of 20) was added to the CRM protein, and the solution was mixed.
c. Sodium cyanoborohydride (0.5 g/ml) (10× molar excess) was added, and the solution was mixed and incubated at 37° C. for 3 days.
d. Sodium borohydride solution (100× the reducing groups) was added, and the solution was allowed to stand at room temperature for 2 hours.
e. The conjugate was diluted 10× with 6M urea to dissolve any precipitate, and the solution was ultrafiltered using an Amicon stirred cell with a YM-30 (30,000 Mw cut-off) membrane.
f. The solution was repeatedly ultrafiltered using sterile saline until the filtrate was negative for pentose and cyanide ion.

Properties of the Final Conjugates

Table 11 presents various characteristics of the PRP-$CRM_{197}$ conjugates from various batches of oxidized PRP and lots resulting from several conjugation runs:

TABLE 11

| | PRODUCTS OF CRM-PRP CONJUGATION | | | |
|---|---|---|---|---|
| VACCINE LOT NO. | PRP SACCHARIDE BATCH | RATIO OF PRP/CRM IN REACTION MIXTURE (μg/μg) | RATIO OF PRP/CRM IN FINAL CONJUGATE (μg/μg) | Kd* (SEPHAROSE CL-4B) |
| 5 | #2 | 1.0 | 0.25 | 0.27 |
| 6 | #2 | 2.0 | 0.62 | 0.31 |
| 7 | #3 | 1.0 | 0.38 | 0.36 |
| 8 | #3 | 2.0 | 0.57 | 0.44 |
| 9 | #6 | 1.0 | 0.60 | 0.48 |
| 10 | #6 | 2.0 | 0.42 | 0.48 |
| 11 | #7 | 1.0 | 0.27 | 0.30 |
| 12 | #7 | 2.0 | 0.42 | 0.48 |

*Kd at which 50% of the material (protein) elutes.

Bottling a. The CRM-PRP conjugate is sterile filtered through a 0.8 and then a 0.22 micron filter into a tared sterile container.
b. A sample is removed aseptically and analyzed for protein by Lowry assay.
c. The volume of filtered material is determined by weighing the container and a final volume calculated to give 50 μg of protein per ml.
d. An amount of 1% Thimerosal in sterile saline is added through a sterile 0.22 micron filter to give 0.01% Thimerosal in the final solution.
e. The vaccine is brought to the final volume with sterile saline filtered through a 0.22 micron filter.
f. The solution is mixed and 5.5 ml aliquoted into sterile, pyrogen-free 10 ml vials (Wheaton, type 1 glass), which are stopped (butyl gray rubber, Wheaton), sealed, and stored at 2°–8° C.

| FINAL DOSAGE FORMULATIONS* | | | |
|---|---|---|---|
| Vaccine Lot No. | Protein (μg/ml) | PRP (μg/ml) | Kd** |
| 5 | 50 | 12.5 | 0.27 |
| 6 | 50 | 31.0 | 0.31 |
| 7 | 50 | 19.0 | 0.36 |
| 8 | 50 | 28.5 | 0.44 |
| 9 | 50 | 30.0 | 0.48 |
| 10 | 50 | 21.0 | 0.48 |
| 11 | 50 | 13.5 | 0.30 |

| -continued | | | |
|---|---|---|---|
| FINAL DOSAGE FORMULATIONS* | | | |
| Vaccine Lot No. | Protein (μg/ml) | PRP (μg/ml) | Kd** |
| 12 | 50 | 21.0 | 0.48 |

*All formulations are made up in 0.9% NaCl and 0.01% Thimerosal.
**Kd at which 50% of the material (protein) elutes.

Testing In Vitro Antigenicity

Serial dilutions of vaccine in PBS 0,05% Tween were added in duplicate to wells of microtiter plates precoated with diphtheria toxoid, A pooled high-titered polyclonal human diphtheria antitoxin serum or a human polyclonal anti-PRP serum was then added to the wells and the plates incubated at 20° C. for 24 hours. Antibody binding was determined by subsequent incubation of the wells with enzyme-labelled anti-human immunoglobulin followed by incubation for 60 minutes with the enzyme substrate and quantitation of the optical density. The results are presented in Table 12.

TABLE 12

In Vitro Antigenicity of PRP-CRM Conjugate
Inhibition of Binding of Human Polyclonal
Anti-Diphtheria Toxoid and Anti-PRP Antibodies

| | EQUIVALENT OF INHIBITOR ON BINDING | |
|---|---|---|
| VACCINE | ANTI-PRP | ANTI-DIP TOXOID |
| PRP | (1) | — |
| DT-Mass* | — | (100) |
| Lot #5 | 1.5 | 87.0 |
| Lot #6 | 1.1 | 57.0 |
| Lot #7 | 3.3 | 9.3 |
| Lot #8 | 2.9 | 8.0 |

*Diphtheria toxoid supplied by the Massachusetts Public Health Biologic Laboratories, lot Dcp 27.

The data in Table 12 indicate that the various lots of vaccine retain in vitro antigenicity: they can compete with polyclonal antibodies to PRP and to diphtheria toxoid. The data also indicate that the PRP antigen is relatively exposed while the diphtheria toxoid epitopes are less well and variably exposed.

Immunogenicity in Animals a. Rabbits

Table 13 summarizes three experiments in which young rabbits were vaccinated at week 0, 1, and 2 with 25 μg of vaccine. All vaccines were immunogenic and gave boostable anti-PRP responses as determined by ELISA assay. Moderate anti-PRP responses were seen even after a single injection of 25 μg of conjugate vaccine.

b. Mice

The results obtained with vaccination of young Swiss Webster mice again produced a boostable anti-PRP response (data not shown)

TABLE 13

ANTI-PRP RESPONSES IN WEANLING RABBITS
TO VARIOUS LOTS OF PRP-CRM CONJUGATES

| VACCINE LOT NO. | WEEK 0 μg/ml (GMT) | WEEK 1 μg/ml (GMT) | WEEK 3 μg/ml (GMT) |
|---|---|---|---|
| 5 | 0.1 | 0.23 | 7.56 |
| 6 | 0.1 | 0.38 | 2.86 |
| 7 | 0.2 | 0.86 | 9.70 |
| 8 | 0.1 | 0.87 | 7.61 |
| 9 | 0.1 | 0.36 | 3.88 |
| 10 | 0.1 | 0.92 | 1.84 |
| 11 | 0.1 | 0.21 | 5.01 |
| 12 | 0.1 | 0.31 | 2.33 |

Immunogenicity in Human Infants

Infant subjects were healthy and had no prior immunization with Hib vaccine nor history of serious adverse reaction to vaccines. Beginning at the ages noted in Table 14 (18, 7 and 2 mo., respectively), they were bled, given a 25 μg subcutaneous primary injection of PRP-CRM conjugate, observed at least 20 minutes and released to their parents for observation and recording of possible local and systemic adverse reactions.

For the 7-mo. and 2-mo. groups, after lapse of the times indicated in Table 14, the process was repeated for a secondary immunization with the same vaccine. After another lapse of time (see Table 14), they were again bled for determination of the secondary response.

As can be seen from Table 14, single injections were effective in raising antibodies in age groups 18 and 7 months, while in 2 month old infants a modest increase in antibody was observed (despite the expected decline in maternal IgG antibodies). In all of the infants, adequate levels of anti-PRP antibody were observed 1-2 months after a second immunization. The response observed in 6 month old infants after two immunizations was sufficient to elicit protective levels of antibodies.

TABLE 14

ANTI-PRP ANTIBODY RESPONSE
to 25 μg VACCINE

| Age (mos.) at Vaccination | No. of Children | Antibody, μg/ml* Pre | Post 1 | Post 2 |
|---|---|---|---|---|
| 18-23 | 84 | 0.40 1 mo. | 6.53 | |
| 7-15 | 88 | 0.15 1-2 mo. | 4.54 1-2 mo. | 18.9 |
| 2-6 | 30 | 0.17 2 mo. | 0.25 2 mo. | 1.23 |

*Geometric Mean Titer.

EXAMPLE: COUPLING OF PERIODATE-OXIDIZED PNEUMOCOCCAL POLYSACCHARIDES TO DIPHTHERIA TOXOID

Table 15 presents a summary of several experiments in which periodate-oxidized pneumococcal polysaccharides were coupled to diphtheria toxoid. The pneumococcal capsular polysaccharides (PnPS) of the types indicated in the table were reacted for 90 minutes at 37° C. with the indicated amount of sodium periodate, and then recovered by filtration on a Centricon-10 ultrafiltration device (Amicon).

The oxidized PS were reacted with 4mg of purified toxoid lot Dcp 27 and 10 mg of $NaCNBH_3$ in a total volume of 0.75 ml for 3 days at 37° C. at pH 8. The protein fraction was recovered by precipitation and washing with 90% saturated ammonium sulfate. The Pn PS antigenic equivalence was assayed by radioantigen binding inhibition using human antiserum to Pn PS and $^{14}C$ labeled Pn PS.

TABLE 15

Coupling of Periodate-Oxidized
Pneumococcal Polysaccharides (Pn PS) to
Diphtheria Toxoid by Reductive Amination

| Pn PS type | μmol $IO_4$ reacted with 10 mg PS | Pn PS antigenic activity recovered in protein fraction after coupling reaction (μg PS/μg protein) |
|---|---|---|
| 3 | 50 | 0.1 |
| 6A | 4 | 0.2 |
| 12 | 4 | 0.1 |
| 14 | 6 | 0.1 |
| 23 | 4 | 0.1 |

Having described the invention with particular reference to certain embodiments, it will be obvious to those skilled in the art to which the invention pertains after understanding the invention, that various changes and modifications may be made without departing from the spirit and scope of the invention as defined by the appended claims.

We claim:

1. An immunogenic conjugate comprising the reductive amination product of an intact capsular polymer of the bacterial pathogen *Streptococcus pneumoniae* having at least two carbonyl groups and a bacterial toxin or toxoid, said conjugate comprising a cross-linked conjugate in which there is a direct covalent linkage between the capsular polymer and the toxin or toxoid.

2. The immunogenic conjugate of claim 1, in which the bacterial pathogen is *Streptococcus pneumoniae* serotype 3.

3. The immunogenic conjugate of claim 1, in which the bacterial pathogen is *Streptococcus pneumoniae* serotype 12.

4. The immunogenic conjugate of claim 1, in which the bacterial pathogen is *Streptococcus pneumoniae* serotype 14.

5. The immunogenic conjugate of claim 1, in which the bacterial pathogen is *Streptococcus pneumoniae* serotype 23.

6. The immunogenic conjugate of claim 1, in which the toxin or toxoid is diphtheria toxin or toxoid.

7. The immunogenic conjugate of claim 6, in which the toxoid is $CRM_{197}$.

* * * * *